(12) United States Patent
Bair

(10) Patent No.: US 6,527,766 B1
(45) Date of Patent: Mar. 4, 2003

(54) INSTRUMENT AND METHOD FOR PHACOEMULSIFICATION BY DIRECT THERMAL IRRADIATION

(75) Inventor: Scott Bair, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 09/560,020

(22) Filed: Apr. 27, 2000

Related U.S. Application Data

(60) Provisional application No. 60/131,443, filed on Apr. 28, 1999.

(51) Int. Cl.$^7$ ............................................... A61B 18/04
(52) U.S. Cl. ........................................................ 606/28
(58) Field of Search .............................. 606/27, 28, 29, 606/41, 48, 49, 50; 604/35

(56) References Cited

U.S. PATENT DOCUMENTS

| | | | |
|---|---|---|---|
| 4,019,514 A | 4/1977 | Banko | 128/230 |
| 4,955,883 A | 9/1990 | Nevyas et al. | 606/28 |
| 5,257,988 A | 11/1993 | L'Esperance, Jr. | 606/6 |
| 5,616,120 A | * 4/1997 | Andrew et al. | 604/28 |
| 5,865,790 A | 2/1999 | Bair | 604/35 |
| 5,989,212 A | 11/1999 | Sussman | 604/27 |
| 5,997,499 A | 12/1999 | Sussman | 604/27 |
| 6,066,138 A | * 5/2000 | Sheffer et al. | 606/49 |

FOREIGN PATENT DOCUMENTS

| | | |
|---|---|---|
| EP | 0 448 857 A1 | 10/1991 |
| WO | WO 96/24314 | 8/1996 |

* cited by examiner

*Primary Examiner*—Edward K. Look
*Assistant Examiner*—Michael Leslie
(74) *Attorney, Agent, or Firm*—Sherry M. Knowles, Esq.; Clark G. Sullivan, Esq.; King & Spalding

(57) ABSTRACT

A phacoemulsification and aspiration device comprising: (a) a substantially hollow housing comprising a first end and a second end; (b) an electrical resistance heating element disposed at the first end of the housing and configured to thermally irradiate a space proximal to the first end and exterior to the housing; (c) a source of electricity in electrical contact with the heating element; and (d) a vacuum source disposed at and integrally connected to the second end of the housing; and a method for treating cataracts in vivo by liquefying a cataractous lens nucleus and aspirating the same from within a surrounding lens capsule comprising the steps of: (a) thermally irradiating and liquefying a lens; and (b) aspirating the lens.

14 Claims, 1 Drawing Sheet

INSTRUMENT AND METHOD FOR PHACOEMULSIFICATION BY DIRECT THERMAL IRRADIATION

CROSS REFERENCE TO RELATED APPLICATIONS

This application claims priority to U.S. Provisional Application No. 60/131,443, filed Apr. 28, 1999.

FIELD OF THE INVENTION

This invention relates generally to phacoemulsification devices and methods for liquefying and aspirating lens nuclei in vivo.

BACKGROUND OF THE INVENTION

A cataract is an opacity or clouding of the lens, the elliptical, normally transparent structure that sits behind the pupil of the eye. The lens of the eye focuses light rays into images on the retina, the photosensitive tissue at the back of the eye. The lens of an adult human eye is about 9 millimeters in diameter and about 5 millimeters thick. The lens consists of an inner nucleus and an outer cortex; it is surrounded by a cellophane-like capsule which is the basement membrane of the lens epithelial cells. In young people the lens is elastic and changes shape easily, allowing the eyes to focus clearly on both nearby and distant objects. Aging and other factors may cause the proteins of the lens nucleus to clump together, forming opaque (cloudy) areas known as nuclear cataracts.

According to the World Health Organization, cataracts are the leading cause of blindness around the world; an estimated 17 million people are blind because of them. In the U.S., where surgery has greatly reduced this risk, tens of thousands still lose their sight from this condition, and millions more have poor vision because of cataracts.

A typical procedure for treating cataracts is called extracapsular cataract extraction, in which the surgeon removes the central portion (the nucleus) of the lens but leaves the capsular bag in place, which adds structural strength to the eye and enhances the healing process. Less commonly, in intracapsular cataract extraction, the surgeon removes the lens and the entire capsule. There are greater risks with this procedure for swelling and retinal detachment. In both procedures the ophthalmologist works under an operating microscope to make a small incision in the cornea of the eye and then extracts the clouded lens through this incision; a replacement lens is then usually inserted.

With the clouded lens removed, the eye cannot focus a sharp image on the retina, and a replacement lens is needed. In about 90% of cataract operations an artificial lens, known as an intraocular lens (IOL), is inserted. In the remaining 10%, a new lens is not implanted; rather, the patient relies solely on corrective eyeglasses or contact lenses. During the most common cataract operations, the surgeon inserts the artificial lens into the capsular bag where the natural lens used to be.

In extracapsular lens removal, the anterior portion of the capsule is cut open so that the cataractous lens can be removed. However, the equatorial and posterior portions of the lens capsule are left intact. Once the cataractous lens nucleus and cortex are removed, the implant can be inserted therein. In traditional extracapsular cataract extraction, the lens nucleus is removed manually. A drawback of this is that a relatively large incision (from 8 mm to 11 mm) must be made in the limbus in order to remove the cataractous lens. That large of an incision causes a relatively lengthy post-operative healing time and is often the cause of significant surgically-induced post-operative astigmatism.

Ultrasonic phacoemulsification (phaco means lens), a version of extracapsular surgery, is now the most common cataract procedure in the United States. The ophthalmologist removes the clouded lens by using ultrasound to break it up into fragments so small they can be aspirated out with a suction device. A replacement lens is then usually inserted. The incision is much smaller than that made in conventional surgery and may not require a suture if the opening is watertight. A suture may be required if a tear or break occurs during the procedure or if an unfoldable lens is inserted that requires a wider incision.

In ultrasonic phacoemulsification the ultrasonic tip, which is rather sharp and made of metal, vibrates approximately 40,000 times per second in order to break up the lens nucleus into tiny pieces so that these pieces can then be aspirated from the eye. The advantage of phacoemulsification is that it allows lens nucleus removal through a relatively small incision of about 3 mm. The disadvantage, however, is that it has proven to be relatively dangerous since the ultrasonic tip destroys any and all tissue that gets in its way. If the vibrating tip comes into contact with the cornea, iris, or capsule, it can cause serious and permanent damage. Moreover, during the break up of the hard nucleus, the tip may contact with and tear the posterior capsule. Another disadvantage of phacoemulsification is that it requires a very high degree of skill, concentration and experience on the surgeon's part for it to be performed well on a consistent basis.

Due to the above, cataract surgeons desire a small incision cataract extraction procedure which is inherently safer and easier to perform than phacoemulsification. U.S. Pat. No. 5,616,120 to Andrews et al. describes a technique for liquefying a hardened cataractous lens by injecting hot water or saline into the capsular bag for emulsification of a cataractious lens within the bag. Once the hot solution heats and liquefies the nucleus, one is able to aspirate the lens and insert a new intraocular lens. The invention has the disadvantage of jetting hot water across the capsule with potential damage to other structures such as zonules and the endothelium.

Therefore, it is an object of the invention to provide a method and apparatus for safely liquefying the hardened nucleus of a lens, so as to allow its removal by aspiration.

It is a still further object of the invention to provide a simplified appartus with which to perform phaocemulsification and aspiration of lens nuclei, to reduce the possibility of accidents and surgeon error.

It is another object of the invention to use heat in order to safely liquefy a hardened lens nucleus before its eventual aspiration.

SUMMARY OF THE INVENTION

The present invention achieves these objectives by localized heating along the edge of an aspiration cannula. The cannula is initially inserted through a small incision in the cornea, or in the limbus, and contacted with the lens. An electrically resistive element is fixed to the tip of the cannula, and generates heat when electricity is passed through it. The heat irradiates the lens, raises the temperature of the lens tissue, and liquefies the lens. Upon liquefication the lens is aspirated.

In accordance with the purpose(s) of this invention, as embodied and broadly described herein, this invention, in one aspect, relates to a phacoemulsification and aspiration device comprising: (a) a substantially hollow housing comprising a first end and a second end; (b) an electrical resistance heating element disposed at the first end of the housing and configured to thermally irradiate a space proximal to the first end and exterior to the housing; (c) a source of electricity in electrical contact with the heating element; and (d) a vacuum source disposed at and integrally connected to the second end of the housing.

In another aspect the invention relates to a method for treating cataracts in vivo by liquefying a cataractous lens nucleus and aspirating the same from within a surrounding lens capsule comprising the steps of: (a) thermally irradiating and liquefying a lens; and (b) aspirating the lens.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE INVENTION

The present invention may be understood more readily by reference to the following detailed description and the examples included therein and to the figures and their previous and following description.

As used in this application, the term liquefy is intended to encompass the concept of gelifaction or emulsification. That is, liquefy or liquefaction implies changing a hardened lens nucleus into a liquid or into a soft enough gel-like substance or slurry or emulsion (suspended particles in liquid) that it can be aspirated from the eye by standard aspiration devices.

In one aspect, the invention relates to a phacoemulsification and aspiration device comprising: (a) a substantially hollow housing comprising a first end and a second end; (b) an electrical resistance heating element disposed at the first end of the housing and configured to thermally irradiate a space proximal to the first end and exterior to the housing; (c) a source of electricity in electrical contact with the heating element; and (d) a vacuum source disposed at and integrally connected to the second end of the housing.

In another aspect the invention relates to a method for treating cataracts in vivo by liquefying a cataractous lens nucleus and aspirating the same from within a surrounding lens capsule comprising the steps of: (a) thermally irradiating and liquefying a lens; and (b) aspirating the lens.

Figure 1:
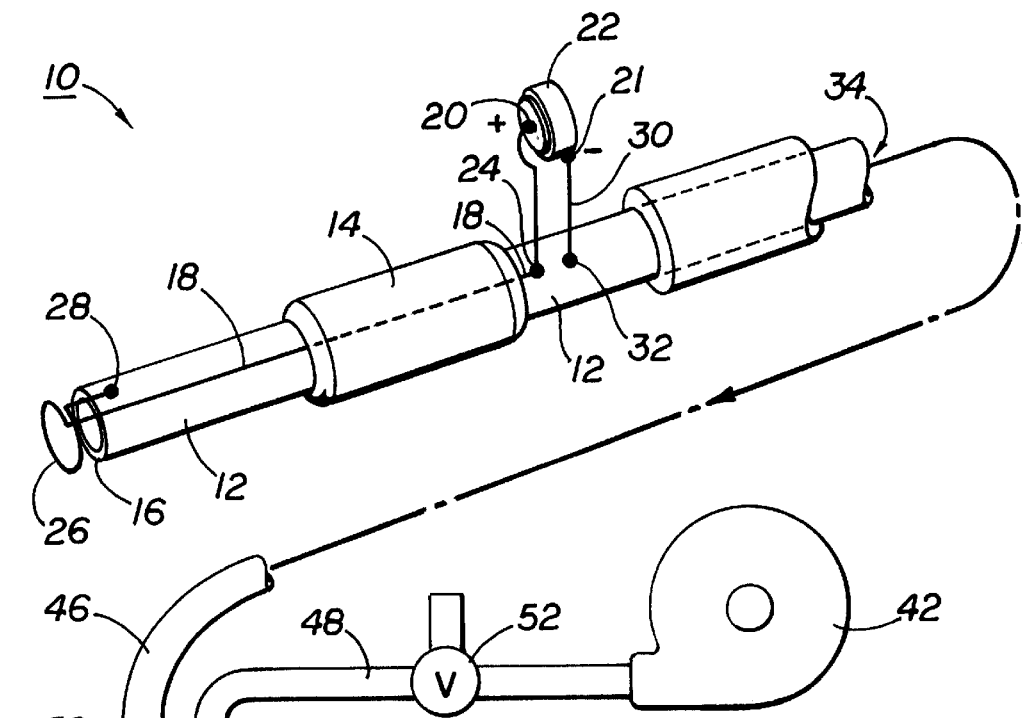
FIG. 1 is an elevational view of a phacoemulsification and aspiration device constructed in accordance with the principles of the present invention.

Referring now to the drawings in detail wherein like reference numerals have been used in the figures to designate like elements, there is shown in FIG. 1 a phacoemulsification and aspiration device constructed in accordance with the principles of the present invention and designated generally as 10. The phacoemulsification device 10 includes an elongated cannula 12 which extends through a hollow handpiece 14 and terminates in a hollow tip 16. An electrically conductive and insulated lead wire 18 is supplied with electricity from the positive terminal 20 of power supply 22, which preferably supplies variable voltage. The lead wire 18 engages the cannula at point 24, traverses the cannula beneath the handpiece 14, and terminates at hollow tip 16. The wire is electrically insulated to prevent direct electrical contact between the lead wire and the cannula, preferably by conventional plenum sheathing. A glue is preferably applied to the lead wire along its entire length to secure it to the cannula as one complete unit.

In FIG. 1, tip 16 is shown as a circular tip having a plane that is perpendicular to the axis of cannula 12. However, tips can assume any configuration that will permit or potentially facilitate the irradiation of a cataractous lens and aspiration of same. For example, in one embodiment the tip is flared outward like a bugle, to increase the area available for suction and heat transfer.

Figure 2:
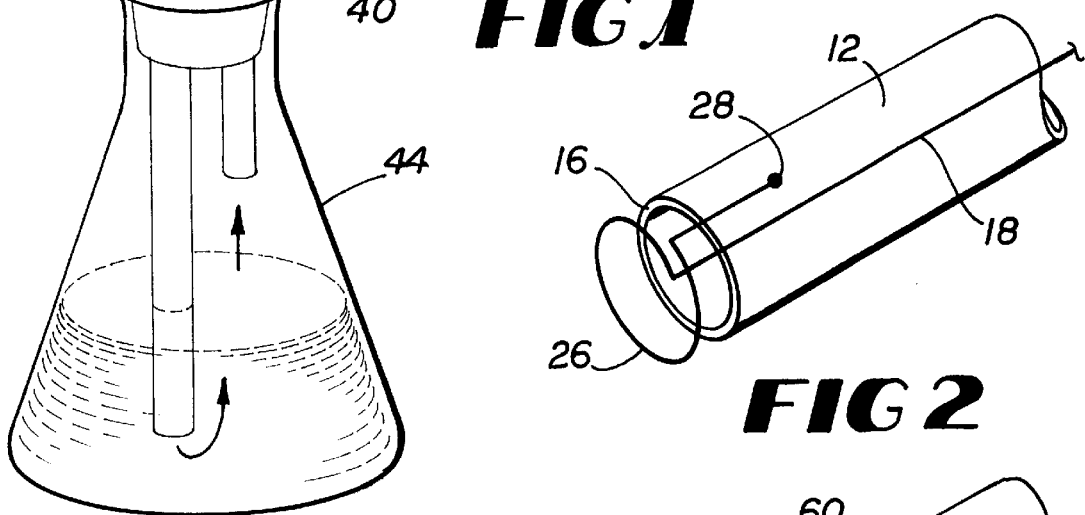
FIG. 2 is an axial view of the tip of the device shown in FIG. 1, showing the placement of the heating coil in relation to the cannula in one embodiment of the invention.

As shown in more detail in FIG. 2, the wire forms a coil 26 about the periphery of the cannula 10 at the tip 16. In the particular embodiment shown in FIG. 2, the coil is offset by a short distance from the tip of the cannula. The coil generally replicates the cross-section of the tip 16, and thus appears generally as an axial extension of the cannula. The coil is preferably fixed to the tip with an appropriate glue or electrically resistant material. Such material might also act to encapsulate the coil, to prevent direct contact between the coil and the lens. Encapsulation can be used, for example, to prevent loss of suction between the coil and the cannula.

The glue or electrically resistant material preferably does not block the irradiation of thermal heat from the coil. Thus, the coil is thermally exposed at the tip of the cannula, in the sense that heat generated by electrical resistance within the coil is allowed to irradiate the surrounding space. It is also important to prevent electrical contact between the coil and the periphery of the cannula prematurely, because such contact would short-circuit the resistive loop created by the coil. Thus, the coil does not make electrical contact with cannula 12 except at electrical contact point 28.

In one embodiment the coil is displaced axially about 0.2 millimeters from the cannula edge for electrical isolation. The single loop is resistively heated by DC current producing about 4 watts of thermal heat. An alternative preferred approach would encapsulate the resistance wire in a material such as ceramic which transmits heat generated by the coil, but does not conduct electricity from the coil. The ceramic encapsulated coil would then form the edge of the cannula.

Figure 3:
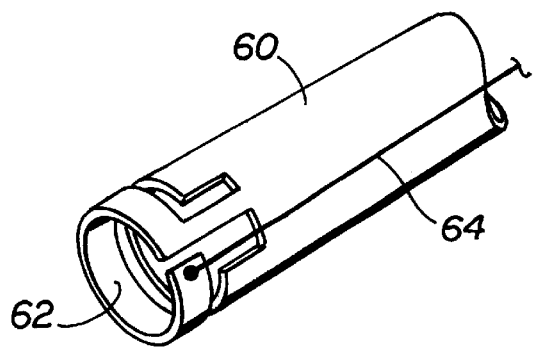
FIG. 3 is a perspective view of a portion of a cannula constructed in accordance with this invention, showing in detail an alternative tip.

FIG. 3 displays an alternative tip for devices of the present invention, in which the heating element is formed from the cannula. In particular, a circular ribbon 62 is cut out of the tip of cannula 60, and protrudes from the tip. A lead wire 64 supplies electricity to the circular ribbon 62, for generating heat in the ribbon. Electricity returns to the electrical supply through the contact between the ribbon 62 and cannula 60.

Thus, in one aspect the invention provides a device in which the electrical resistance heating element comprises a coil of wire that is axially and proximally displaced from the first end of the housing, wherein the cross section defined by the coil approximates the cross section of the first end of the housing. In other words, the coil has a geometry such as a circle that has the same dimensions as the cross section of the housing; the plane of the coil is parallel to the plane of the cross section; and the center of the coil is circle is aligned with the central axis of the housing.

The cannula is formed of an electrically conductive material, and an electrical circuit is formed across the cannula from electrical contact point 23 to a second electrical contact point 32. A second wire 30 is in electrical contact with the cannula at electrical contact point 32, and connects electrical contact point 32 to the negative terminal 34 of battery 22 thereby completing the electrical circuit. A device for regulating the flow of electricity to the coil 26 may be inserted at any point between the electrical source and the coil, to modulate the voltage supplied to the coil. Moreover, it will be understood that the electrical source can supply alternating or direct current.

The heat generated by the wire at coil 26 is a direct function of the internal resistance of the coil, and the voltage of electricity supplied to the coil, and is governed by the equation:

Heat (Joules/second)=$V^2$/R where V is voltage, and R is resistance (measured in ohms). The resistance R is a function of the resistivity constant for the material used to form the wire, the length of the coil wire, and the cross-section of coil wire.

The heat generated by the wire at coil 26 is important because it determines the time within which the lens liquefies, and the time required to perform the phacoemulsification and aspiration procedure. While it is generally desirable to maximize the amount of heat to reduce the time of the procedure, an excessive amount of heat should not be used because an excess of heat could harden the proteinaceous structure of the lens before the lens can be aspirated and prevent the hardened portion of the lens from reaching a liquid state. Such hardening is comparable to the cooking of an egg. It has been mathematically determined using various assumptions that 1.2 watts of energy applied to a coil having a resistance of 0.6 ohms produces an average temperature increase in the lens of roughly 1 degree celcius every four seconds. The temperature of the lens proximate to the heating element will, of course, increase more rapidly than the average.

As the lens is liquefied it is aspirated through the cannula. Aspiration of liquefied tissue occurs through the bore of the cannula by connection to a reservoir for catching the tissue and a vacuum pump. The vacuum also maintains contact between the lens and the hot tip during the procedures. In the embodiment shown in FIG. 1, the cannula has an opposite end 34 connected to a vacuum source 40. The vacuum source 40 comprises a pump 42, a reservoir 44, an aspirating tube 46, and a suction tube 48. The aspirating tube 46 and suction tube 48 enter the reservoir 44 through a sealed opening 50. The opening can be sealed by conventional devices such as corks and rubber stoppers. A vacuum is created in the reservoir by vacuum pump 42 through suction tube 48, and modulated by a bleed valve 52. The bleed valve can be controlled by a foot pedal or other method known generally in the art. The level of vacuum supplied to the tip 16 of the cannula is generally in accord with phacoemulsification devices of the prior art. Generally, sufficient vacuum should be supplied to aspirate the lens upon liquefaction, but not too much vacuum so as to cause collapse of the capsule during flow surges.

Various configurations can be employed to effect the electrical connections needed to carry out the invention. In the embodiment displayed in FIGS. 1 and 2, the invention provides a phacoemulsification and aspiration device wherein the source of electricity and electrical resistance heating element form an electrical circuit which comprises:
  a) a source of DC or AC electricity comprising first and second terminals;
  b) one or more wires which are integrated electrically, and which are in electrical contact with the first terminal of the source of DC or AC electricity and a first end of the heating element; and
  c) one or more wires which are integrated electrically, and which are in electrical contact with a second end of the heating element and the second terminal of the source of DC or AC electricity.

In another aspect the invention provides a phacoemulsification and aspiration device wherein the source of electricity and electrical resistance heating element form an electrical circuit which comprises:
  a) a source of DC or AC electricity comprising first and second terminals;
  b) an electrically insulated wire which is in electrical contact with the first terminal of the source of DC or AC electricity, and which traverses the housing and makes electrical contact with a first end of the heating element;
  c) an electrical contact between a second end of the heating element and the housing; and
  d) a second electrically insulated wire that contacts the housing and the source of DC or AC electricity.

Various other configurations are, of course possible, including those in which (1) the first and/or second wires are not insulated, (2) the first wire does not traverse the housing, (3) the second end of the heating element contacts the source of electricity directly without forming an electrical circuit through the housing, and/or (4) more than one wire is used to connect the first or second terminal to the first or second end of the heating element. The latter embodiment in which more than one wire is used to connect the electrical terminal (s) and the heating element, is especially envisioned because it would allow direct measurement and control of the electrical resistance of the heating element. By correlating resistance to temperature behavior, one is able to control the element temperature precisely and optimally.

In particular, one could construct the device to measure the voltage drop and current across the heating element. The voltage drop and current could then be used to calculate temperature in several ways. For example, the device could be calibrated based upon a known relationship between temperature and voltage drop and current for the particular heating element in a relevant medium such as water, and be able to calculate the temperature upon measurement or knowledge of the voltage drop and current across the element. Alternatively, the voltage drop and current could be used to measure the resistivity of the heating element material, and the device calibrated based upon a known relationship between the temperature and resistivity of the heating element material. If desired the device could display the temperature of the element for the benefit of the user.

Using appropriate temperature feedback controls integrated with the voltage or current controls, one could use this structure to adjust the temperature of the heating element, or to set it at a constant level. One could similarly measure the temperature of the heating element directly with the aid of a thermometer disposed close to the heating element, and use appropriate feedback controls to adjust the voltage or current supplied to the heating element, and thereby to control the temperature of the heating element.

The term "integrated electrically" means that a current of electricity can flow continuously between the wires, even though the wires may be physically disconnected from one another by an electrical component such as a voltage regulator or the housing. The term "wire" is meant to encompass cables, rods, and similar configurations of electrically conductive materials. The first and second ends of the electrically resistive heating element refer to the points on the element where electrical contact is made with the wires that form the electrical circuit, and thus which define the "ends" of the electrical circuit through the element.

To facilitate an understanding of the principles associated with the foregoing arrangement, its operation will now be briefly described. The device and method are most applicable to the liquefication and aspiration of cataractous lenses. Such lenses are surrounded by a lens capsule. A small incision is made in the cornea, or in the limbus, to allow the tip 16 of the cannula 12 to be inserted therein. An opening is also made in the lens capsule. The cannula 12 is passed through the anterior chamber and through the opening in the lens capsule, so that the tip 16 of the cannula is placed in contact with the cataractous lens nucleus.

The coil 26 at tip 16 is also in physical contact with the lens. Thus, when electricity is supplied to the device, the coil 26 at tip 16, which is made of electrically resisting material, generates heat that is transmitted or irradiated directly to the surrounding lens tissue. Upon contact with the heat, the temperature of the cataractous lens rises and the lens liquefies.

The liquefied lens is aspirated through the cannula 12 and through the aspirating tube 46 by the vacuum source 40, which preferably applies vacuum substantially throughout the procedure. It is believed that it is not necessary or desirable to liquefy the entire lens nucleus before aspirating the same. Rather, as a portion of the lens nucleus is liquefied by the heated solution, it is aspirated. This process continues until the entire lens nucleus has been liquefied and aspirated. Once the lens nucleus and cortex are evacuated from the lens capsule, an intraocular lens implant can be inserted through a small enlargement of the incision and the opening in the lens capsule.

EXAMPLE 1

In an experiment a 3 mm cannula (o.d.) was outfitted with a 0.25 mm diameter platinum wire fixed about 0.5 mm from the cannula end opening. The wire formed a loop of approximately the same (3 mm) diameter as the cannula and was fixed by soldering one end of the platinum wire to the stainless steel cannula and the other to a copper stand-off. DC current was supplied at 1.6 volts to the loop of platinum which has a measured resistance of 0.6 ohms. An expressed lens from a pig eye was placed in a dish and submerged under one centimeter of water. At the end opposite to the hot wire, the cannula was connected to a hose leading to a reservoir and vacuum pump. With the vacuum pump not operating, the hot wire easily sculpted the porcine lens by manual manipulation of the instrument. The pump was started and the hot wire loop placed against the lens, the instrument immediately cored through the lens and the remaining tissue was aspirated within three seconds. Fragments and one long (about 6 mm) core were found in the reservoir.

EXAMPLE 2

In example 2, the instrument of example 1 was modified by encapsulating the resistance wire with ceramic filled epoxy. The encapsulation prevents leakage of liquid (water) between the heating wire and the cannula. An expressed human cataract, which is harder than a pig lens, was placed in a dish and submerged. The aspiration vacuum was regulated to 65 mm of mercury. First, 1.5 v was supplied and the cataract was aspirated in 50 seconds. A second cataract was aspirated in 3 seconds when 1.75 v was supplied.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A phacoemulsification and aspiration device comprising:
    a) a substantially hollow housing comprising a first end and a second end;
    b) an electrical resistance heating element disposed at the first end of the housing and configured to thermally irradiate a space proximal to the first end and exterior to the housing;
    c) a source of electricity in electrical contact with the heating element; and
    d) a vacuum source disposed at and integrally connected to the second end of the housing.

2. The device of claim 1 wherein the electrical resistance heating element comprises a coil of wire that is axially and proximally displaced from the first end of the housing.

3. The device of claim 1 wherein the electrical resistance heating element is configured in relation to the housing to directly contact a lens when the first end of the housing is brought into contact with the lens.

4. The device of claim 1 wherein the source of electricity comprises an electrically conductive wire that traverses the length of the housing.

5. The device of claim 1 wherein the source of electricity and electrical resistance heating element form an electrical circuit which comprises:
    a) a source of DC or AC electricity comprising first and second terminals;
    b) a first set of one or more wires which are integrated electrically, and which are in electrical contact with the first terminal and a first end of the heating element; and
    c) a second set of one or more wires which are integrated electrically, and which are in electrical contact with a second end of the heating element and the second terminal.

6. The device of claim 1 wherein the source of electricity and electrical resistance heating element form an electrical circuit which comprises:
    a) a source of DC or AC electricity comprising first and second terminals;
    b) a first electrically insulated wire which is in electrical contact with the first terminal of the source of DC or AC electricity, and which traverses the housing and makes electrical contact with a first end of the heating element;
    c) an electrical contact between a second end of the heating element and the housing; and
    d) a second electrically insulated wire that contacts the housing and the source of DC or AC electricity.

7. The device of claim 1 further comprising a vacuum regulator.

8. The device of claim 1 further comprising an electricity regulator.

9. A method for treating cataracts in vivo by liquefying a cataractous lens nucleus and aspirating the same from within a surrounding lens capsule comprising the steps of:
   a) thermally irradiating and liquefying a lens by:
      i) providing a hollow housing comprising a first end and a second end;
      ii) contacting an electrically resistive element disposed at the first end of the hollow housing with the lens; and
      iii) creating an electrical potential across the element; and
   b) aspirating the lens.

10. The method of claim 9 further comprising supplying a vacuum to a second end of the hollow housing and thereby aspirating the lens nucleus.

11. The method of claim 9 wherein a vacuum is supplied to the second end of the hollow housing continuously during the thermal irradiation of the lens.

12. The method of claim 9 further comprising measuring the voltage drop and current across the electrically resistive element; and converting the voltage drop and current to a temperature for the heating element.

13. The method of claim 12, further comprising modulating the electrical potential across the electrically resistive element in response to the temperature of the electrically resistive element.

14. The method of claim 12, further comprising displaying the temperature of the electrically resistive element.

* * * * *